US010137075B2

(12) United States Patent
Fiorini Puybaret

(10) Patent No.: US 10,137,075 B2
(45) Date of Patent: Nov. 27, 2018

(54) COSMETIC USE OF AN EXTRACT OF BALANITES ALMONDS TO IMPROVE HAIR STRENGTH

(71) Applicant: PIERRE FABRE DERMO-COSMETIQUE, Boulogne-Billancourt (FR)

(72) Inventor: Christel Fiorini Puybaret, Toulouse (FR)

(73) Assignee: PIERRE FABRE DERMO-COSMETIQUE, Boulogne-Billancourt (FR)

(*) Notice: Subject to any disclaimer, the term of this patent is extended or adjusted under 35 U.S.C. 154(b) by 134 days.

(21) Appl. No.: 14/385,088

(22) PCT Filed: Mar. 15, 2013

(86) PCT No.: PCT/EP2013/055426
§ 371 (c)(1),
(2) Date: Sep. 12, 2014

(87) PCT Pub. No.: WO2013/135875
PCT Pub. Date: Sep. 19, 2013

(65) Prior Publication Data
US 2015/0023902 A1 Jan. 22, 2015

(30) Foreign Application Priority Data
Mar. 15, 2012 (FR) ...................... 12 52337

(51) Int. Cl.
*A61K 36/889* (2006.01)
*A61K 8/97* (2017.01)
*A61Q 5/00* (2006.01)
*A61K 36/185* (2006.01)
*A61Q 5/02* (2006.01)
*A61Q 19/00* (2006.01)

(52) U.S. Cl.
CPC .............. *A61K 8/97* (2013.01); *A61K 36/185* (2013.01); *A61Q 5/00* (2013.01); *A61Q 5/002* (2013.01); *A61Q 5/02* (2013.01); *A61Q 19/00* (2013.01); *A61K 2236/30* (2013.01); *A61K 2800/70* (2013.01)

(58) Field of Classification Search
None
See application file for complete search history.

(56) References Cited

U.S. PATENT DOCUMENTS 5,792,448 A * 8/1998 Dubief ................... A61K 8/498
424/701
5,800,818 A 9/1998 Prugnaud et al.
2008/0287662 A1* 11/2008 Wiesman ................. C07J 71/00
536/4.1

FOREIGN PATENT DOCUMENTS

EP 0781545 A1 7/1997
FR 2962907 A1 1/2012

OTHER PUBLICATIONS

Chothani et al. (2011) Pharmacogn. Rev. Jan.-Jun. 5(9): 55-62.*
Gardette et al. (2013) Chemistry and Physics of Lipids 170-171: 1-7.*
Raskin et al. (2004) Current Pharmaceutical Design, 10, 3419-3429.*
Revilla et al. (1998) J. Agric. Food Chem. 46, 4592-4597.*
Abdel-Rahim et al., "Biochemical Dynamics of Hypocholesterolemic Action of Balanites Aegyptiaca Fruit", Food Chemistry, vol. 20, XP-2686854, 1986, pp. 69-78.
Al Ashaal et al., "Phytochemical investigation and medicinal evaluation of fixed oil of Balanites aegyptiaca fruits (Balantiaceae)", Journal of Ethnopharmacology, vol. 127, 2010 (Available online Oct. 13, 2009), XP-26853075, pp. 495-501.
Chapagain et al., "Variation in diosgenin level in seed kernels among different provenances of Balanites aegyptiaca Del (Zygophyllaceae) and its correlation with oil content", African Journal of Biotechnology, vol. 4, No. 11, Nov. 2005, XP-8157777, pp. 1209-1213.
French Search Report dated Dec. 3, 2012, for French Application No. 1252337.
International Search Report and Written Opinion of the International Search Authority, dated , May 7, 2013, for International Application No. PCT/EP2013/055426.
Kibio, "Intense Moisturizing Oil", Mintel, Jun. 2009, XP-2686857, pp. 1-4.
Kusch et al., "In Vitro and In Vivo Antimalarial Activity Assays of Seeds from Balanites aegyptiaca: Compounds of the Extract Show Growth Inhibition and Activity against Plasmodial Aminopeptidase", Journal of Parasitology Research, vol. 2011, Article ID 368692, Mar. 20, 2011, XP-2686855, pp. 1-9.
Laboratoires Kiorane, "Shampoo", Mintel, Oct. 2012, XP-2686858, pp. 1-4.
Laboratoires Phytosolba, "Emulsion Color", Mintel, Jun. 2007, XP-2686853, pp. 1-5.
Natural Beauty Indùstria de Cosméticos, "Leave-In Combing Cream", Mintel, Feb. 2012, XP-2686856, pp. 1-2.
Author Pandita Narahari Title of publication—Rajanighantauh Page(s) being submitted—05(p. 04-08) ( Ref.pg. No. of publication:527 ) Publication Date—Edn. 2nd 1998 Publisher—Indradeo Tripathi; Krishnadas Academy Place of Publication—Varanasi, India.†
Author Mohammad Najmul Ghani Khan Title of publication—Khazaain-al-Advia, vol. III Page(s) being submitted—05 (p. 09-13) ( Ref.pg. No. of publication:1062 ) Publication Date—1 9 2 6 AD Publisher—Nadeem Yunus Printer / Sheikh Mohd Basheer & Sons. Lahore Place of Publication—Lahore.†

* cited by examiner
† cited by third party

*Primary Examiner* — Christopher R Tate
*Assistant Examiner* — Russell G Fiebig
(74) *Attorney, Agent, or Firm* — Birch, Stewart, Kolasch & Birch, LLP

(57) ABSTRACT

The invention concerns the use of a cosmetic compound to improve hair strength, said cosmetic compound comprising as an active ingredient an extract of *Balanites* almonds.

10 Claims, No Drawings

COSMETIC USE OF AN EXTRACT OF BALANITES ALMONDS TO IMPROVE HAIR STRENGTH

This invention relates in general to compositions for hair and more specifically compositions intended to improve hair strength with an anti-breakage action.

The field of the present invention relates to a new method for upgrading an almond extract of a plant belonging to the *Balanites* genus of the Zygophyllaceae family. Preferentially, this invention relates to the work conducted on the *Balanites aegyptiaca* L. Delile species because of it is easy to procure in Africa. However, this feature is non-limiting and an extract of comparable quality with other species of the *Balanites* genus coming from other countries may also be envisaged. It is possible to cite, for example: *Balanites triflora Tiegh* and *Balanites roxburgghii Planch*.

*Balanites aegyptiaca* is also more commonly called desert date.

*Balanites* is a tropical Afro-Asian genus, with around 25 species, of dry sub-arid regions with mean annual rainfall of between 1000 mm and 200 mm and even 100 mm. Its geographic area of distribution extends from Africa, in the West (Senegal-Mauritania coasts), to Myanmar, in the East. *Balanites aegyptiaca* is present in dry tropical Africa, from Senegal to Sudan, Oriental Africa, from Egypt to Zambia, Arabia and India. It arrived in Asia from the Mediterranean via Egypt. It is one of the most common trees in Senegal.

The desert date is a flat or irregular decurrent crown tree reaching 8 to 9 m in height. It is highly remarkable with its soft falling branches with long alternate or more or less spiral spines.

Its fruit is an ellipsoid drupe of 5×2.5 cm, green and pubescent, turning yellow and more or less glabrous at maturity. A thin skin envelops an edible pulp (which represent 43% of the weight of the fresh fruit) around a hard, ovoid and sharp core, containing the almond.

The high carbohydrate and vitamin content of the fruit justifies its name "desert date". It is well liked by children and adults.

All of the portions of the tree are used in traditional African pharmacopeia.
Roots: Snakebite, anthrax
Bark: Jaundice, yellow fever, syphilis, cough, epilepsy and anxiety
Spines: Leprosy
Leaves: Asthenia, anthrax
Fruits: Rheumatism, gentle laxative
Seeds: Oil used in the form of a pomade and an ointment with numerous drugs.

The almond oil is used as a fat for artisanal soap production.

The prior art in the cosmetic field relates primarily to *Balanites* oil (mention may be made of EP 0 781 545—concerning the hydration of the upper layers of the skin).

Surprisingly and unexpectedly, the applicant has identified an original activity of a *Balanites* almond extract, concerning its anti-breakage properties for hair. This type of activity is especially beneficial for improving hair strength and more specifically for dry, damaged and breaking hair.

Below, the content of the compounds of the extract will be indicated for the extract without any drying medium.

The *Balanites* almond extract according to this invention is characterized in that it comprises wax, amino acids, proteins and total sugars.

In the sense of this invention, "wax" refers to fatty alcohol esters; and "total sugars" refers to the sugar content after hydrolysis of the extract.

Qualitatively, the extract according to this invention differs significantly from oil. In fact, even though certain fatty acids and hydrocarbons are also present in our extract as in oil, waxes, free amino acids, proteins and sugars are absent from the oil. These are the technical features retained in order to differentiate our extract from a *Balanites* oil already used in cosmetics.

The extract used in the context of this invention can be prepared as follows.

The almonds of the desert date seed are preferably extracted by a mixture of water and one or more organic solvents.

The organic solvent can be an alcohol (methanol, ethanol, propanol, isopropanol, butanol, octanol), a ketone (methylethyketone, methylisobutylketone), as well as mixtures thereof.

The extract without a drying medium is obtained with a yield of around 25%. This extract is heterogeneous, consisting of a liquid fatty phase (upper phase, 65%) and a solid phase with a buttery aspect (lower phase, 35%). The addition of an inert medium (such as maltodextrin) can enable a homogeneous extract to be obtained.

The extract can also be stabilized by adding an antioxidant such as, for example, butylhydroxytoluene or alpha tocopherol in amounts of between 0.05 to 1 g % of dry extract.

Characterization of the extract (content expressed as g/100 g of extract without a drying medium):
waxes: from 1% to 10% and preferably 4%
free amino acids: 1% to 5% and preferably 2%
proteins: from 0.5% to 10% and preferably 1 to 5%
total sugars: from 20% to 60% and preferably 28%.

This invention relates to the use of a cosmetic composition for improving hair strength, said cosmetic composition including, as an active principle, a *Balanites* almond extract as described above.

This *Balanites* extract is moreover, in consideration of its chemical composition high in sugar, amino acids and proteins, waxes and fatty acids, particularly nutritious for hair.

The *Balanites* almond extract according to this invention makes it possible to nourish the hair fibre by providing it with elements essential for strength and nutrition, and makes the treated hair more resistant to breakage.

Preferably, the hair being treated is fragile, dry, damaged and breaking.

A significant increase in the breakage stress point has been observed in hair treated with an extract according to the invention.

This invention finally relates to a method for cosmetic treatment of hair intended to improve hair strength with an anti-breakage effect consisting in applying, to the hair, a cosmetic composition containing a *Balanites* almond extract according to the invention.

Preferably, the amount of *Balanites* almond extract is between 0.05 and 5% with respect to the total weight of the composition and, preferably, said amount of extract is between 0.05 and 1% with respect to the total weight of the composition.

The cosmetic composition according to the invention may advantageously be in any galenic form normally used in the cosmetic hair care field for topical use. Preferentially, the topical form may in particular be in the form of a shampoo, a balm, a mask, a gel, a lotion, a foam, a spray or a cream.

Thus products designed to be rinsed out are distinguished from those not designed to be rinsed out.

The cosmetic composition according to the invention also includes conventional cosmetically compatible carriers.

The conventional carriers compatible with the cosmetic hair composition may be any carrier among those known to a person skilled in the art for obtaining a cosmetic composition for topical use in the forms as described above.

The cosmetic composition according to the invention may in particular contain formulation additives and aids, such as surfactants of the emulsifying, cleaning, foaming type, etc., complexing agents, thickening agents, gelling agents, stabilizers, preservatives including antimicrobial agents and antioxidants, conditioners, acidifiers, alkalinizers, softeners, solvents, colouring agents, and fragrances.

The following examples are provided as a non-limiting indication.

EXAMPLE 1

Of Preparation OF Plant Extract According to the Invention 1 kg of *Balanites* almonds are extracted with 10 liters of alcohol with 80% (v/v) reflux for 1 hour under agitation.

After filtration and rinsing of the pomace, the filtrate is concentrated, then dried on 750 g of maltodextrin, then stabilized by adding 0.2% alpha-tocopherol.

The extract is a yellowish powder obtained with a yield of around 100% (p/p).

The extract contains (value expressed without drying medium): 4% wax, 2.1% free amino acids, 1.1 to 5% proteins and 28% total sugars.

EXAMPLE 2

1 kg of *Balanites* almonds are extracted with 10 liters of alcohol (v/v) at room temperature for 2 hours under agitation. After filtration and rinsing of the pomace, the filtrate is concentrated to up to 2 liters (concentrate 1) and stabilized by adding butylhydroxytoluene (BHT).

The alcohol-depleted pomace is extracted with 10 liters of EtOH 80% (v/v). After filtration and rinsing of the pomace, the filtrate is concentrated to up to 2 liters (concentrate 2).

0.8 liter of concentrate 2 is mixed with 0.2 liter of concentrate 1. After adding 750 g of maltodextrin, it is all dried in the Rotavapor.

The extract has a composition similar to that of the extract of example 1.

Examples of Cosmetic Compositions:

EXAMPLE 3

Balm to be Rinsed Out

| | |
|---|---|
| Balanites almond extract | 0.1% |
| Guar hydroxypropyltrimonium chloride | 0.3% |
| Propylene glycol | 0.5% |
| Sclerotium gum | 0.3% |
| Cetearyl alcohol/cetearyl mixture | 2% |
| Inulin lauryl carbamate | 0.25% |
| Cetyl alcohol | 7% |
| Ethylhexyl palmitate | 8% |
| Dicaprylyl carbonate | 2% |
| Hydrolyzed wheat protein | 2% |
| Sorbic acid | 0.3% |
| Salicylic acid | 0.15% |
| Phenoxyethanol | 0.7% |
| Colouring agents | qsf |
| Fragrance | qsf |
| Sodium hydroxide | qsf |
| Purified water | qsf |

EXAMPLE 4

Shampoo

| | |
|---|---|
| Balanites almond extract | 0.1% |
| Hydrolyzed wheat protein | 0.5% |
| PEG-7 glycerol cocoate | 8% |
| Ethoxylated olive oil | 3% |
| (Poly)quaternium-10 | 0.5% |
| Decyl glucoside | 2% |
| Na lauroyl methyl isethionate | 2% |
| Sodium laureth sulfate | 13% |
| Lauryl betaine | 5% |
| Sodium benzoate | 0.4% |
| (Di)sodium EDTA | 0.2% |
| Colouring agents | 0.1% |
| Pearlescent base | 8% |
| Fragrance | qsf |
| Citric acid monohydrate | qsf |
| Sodium chloride desulfate | qsf |
| Purified water | qsf |

EXAMPLE 5

Mask

| | |
|---|---|
| Hydrolyzed wheat protein | 3% |
| Balanites almond extract | 0.2% |
| Salicylic acid | 0.15% |
| Guar hydroxypropyltrimonium chloride | 0.5% |
| Propylene glycol | 1% |
| Behentrimonium chloride | 3% |
| Cetearyl alcohol/cetearyl mixture | 1% |
| Inulin lauryl carbamate | 0.15% |
| Glycol palmitate | 6% |
| Behenic alcohol | 4% |
| Diisopropyl adipate | 10% |
| Castor oil | 3% |
| Phenoxyethanol | 0.7% |
| Sorbic acid | 0.3% |
| Fragrance | qsf |
| Lactic acid | qsf |
| Butylhydroxytoluene | 0.05% |
| Colouring agents | qsf |
| Purified water | qsf |

EXAMPLE 6

Skincare Without Rinsing

| | |
|---|---|
| Balanites almond extract | 0.1% |
| Hydrolyzed wheat protein | 0.1% |
| (Poly)acrylate-13 mixture | 1.5% |
| (Di)caprylyl ether | 5% |
| Castor oil | 5% |
| C14-22 alkyl alcohol mixture | 1.25% |

-continued

| | |
|---|---|
| Guar hydroxypropyltrimonium chloride | 0.3% |
| Propylene glycol | 1% |
| Phenoxyethanol | 0.5% |
| Sorbic acid | 0.2% |
| Butylhydroxytoluene | 0.01% |
| Fragrance | qsf |
| Colouring agent | qsf |
| Purified water | qsf |

EXAMPLE 7

Measurements of Mechanical Properties of the Hair Treated With a *Balanites Aegyptiaca* Almond Extract The mechanical properties of the hair are measured by means of a linear extensometer that applies a tensile force until the hair breaks. Thus, by means of a force sensor, the breakage force can be measured. By taking into account the cross-section of the hair, the breakage force is associated with the cross-section and expressed as the breakage stress point.

Method

Hair Used

Original hair: European type, brown, glued weft dense, colour 5/0, total length 20 cm with 18 cm free. Provided by the Kerling International company (Germany).

And hair made fragile obtained by chemical treatments of the original hair: discoloured by chemical oxidation for 4 hours followed by a 30-minute permanent treatment.

The lock of hair made fragile was cut into a plurality of sub-locks with a width of 0.5 cm (mean weight=270±30 mg). Then, these sub-locks were the subject of the test in an amount of one product tested per sub-lock.

Products Tested

The preparations tested were obtained by using, respectively, 5 g and 0.5 g of extract prepared according to example 1 in suspension in 27% ethanol.

100 mL of 5% date extract in 27% ethanol
100 mL of 0.5% date extract in 27% ethanol
100 mL of 27% ethanol.

Application of the Products

The hair made fragile was treated with the preparations, allowing the locks to soak for 96 hours in the solutions, and agitating them during this time.

The untreated hair made fragile locks were used as a control.

At the end of the treatment, the hair locks were washed for 30 seconds with 3% sodium lauryl sulfate, followed by rinsing in clear water for 1 minute.

Finally, the locks were dried for 24 hours in open air before being subjected to the tests according to the protocol below.

Measurement of Mechanical Properties

The equipment used is a Miniature Tensile Tester 675 (MTT, Diastron, UK) associated with a Laser Scan Micrometer (LSM, Mitutoyu, Japan). The procedure for measurement and analysis of the hair is as follows:

Crimping the individual hair strands with a test length of 30 mm (n=40 hair strands per treatment)
Measuring the cross-section of each hair strand by LSM
Subjecting wetted hair strands (1 hour of soaking in water) to tensile stress until breakage by the MTT.
Constant pull rate=10 mm/mn Analysis of the tensile curve in order to identify and raise the breakage stress point in megapascal (MPa, where 1 Pa=1 N/m$^2$), which indicates the breakage force weighted by the cross-section of the hair strand. The variability in the thickness of the hair studied is thus overcome.

This procedure was used to measure and analyse locks having been treated and also locks not having received any treatment (untreated controls).

Results (n=40 Hair Strands Per Treatment)

The results of the measurements of the breakage stress point are presented in table 1, with mean values for the breakage stress points and corresponding standard deviations. The differences with respect to the untreated control were calculated in the form of percentages.

TABLE 1

| | Breakage stress point in MPa for hair tested as a function of treatment | | |
|---|---|---|---|
| Treatment | Mean breakage stress point (MPa) | Standard deviation | % |
| Untreated control | 51.56 | 11.46 | 0.0 |
| 0.5% date | 55.97 | 7.59 | 8.5 |
| 5% date | 57.67 | 10.00 | 11.8 |

A statistical analysis (Student T test, unpaired, bilateral) of these results was performed with the Student test (threshold 5%)

Treated with 0.5% *Balanites* extract, p=0.0468 (Significant)

Treated with 5% *Balanites* extract, p=0.0131 (Significant)

CONCLUSIONS

Under these experimental conditions, a significant increase in the breakage stress point is observed for the two concentrations of date extracts with respect to the untreated control.

These results indicate a reinforcing effect of the active agent on hair made fragile. Thus, the latter, when they were treated by the extract and subjected to a constant pull rate, break with greater force than that of the untreated hair.

This study made it possible to demonstrate the efficacy of a composition according to this invention on the anti-breakage property of hair.

The invention claimed is:

1. A topical cosmetic composition for improving hair strength comprising an effective amount of a hydro-alcoholic *Balanites* almond extract as an active agent and an effective amount of an added preservative, wherein the *Balanites* almond extract includes the following contents expressed as percentages by weight with respect to the extract without a drying medium:
   waxes: from 1% to 10%,
   free amino acids: 1% to 5%,
   proteins: from 0.5% to 10%, and
   total sugars: from 20% to 60%,
wherein the cosmetic composition is in the form of a shampoo, a balm, a mask, a gel, a lotion, a foam, a spray or a cream.

2. The cosmetic composition according to claim 1, characterized in that the amount of extract is between 0.05 and 5% by weight with respect to the total weight of the composition.

3. The cosmetic composition according to claim 1, characterized in that said extract is a *Balanites aegyptiaca, Balanites triflora Tiegh* or *Balanites roxburgghii Planch* extract.

4. The cosmetic composition according to claim 2, characterized in that said extract is a *Balanites aegyptiaca, Balanites triflora Tiegh* or *Balanites roxburgghii Planch* extract.

5. The cosmetic composition according to claim 1, characterized in that the *Balanites* almond extract includes the following contents expressed as percentages by weight with respect to the extract without a drying medium:
   waxes: 4%
   free amino acids: 2%
   proteins: from 1 to 5%
   total sugars: 28%.

6. The cosmetic composition according to claim 1, characterized in that the *Balanites* almond extract includes the following contents expressed as percentages by weight with respect to the extract without a drying medium:
   waxes: 4%
   free amino acids: 2%
   proteins: from 1 to 5%
   total sugars: 28%.

7. The cosmetic composition according to claim 1, characterized in that said extract is a *Balanites aegyptiaca* extract.

8. A method of improving hair strength comprising applying an effective amount of the composition of claim 1 to the hair of a subject in need thereof.

9. A method of improving hair strength comprising applying an effective amount of the composition of claim 2 to the hair of a subject in need thereof.

10. A method of improving hair strength comprising applying an effective amount of the composition of claim 3 to the hair of a subject in need thereof.

* * * * *